US008535720B2

(12) United States Patent
Shekunov et al.

(10) Patent No.: US 8,535,720 B2
(45) Date of Patent: Sep. 17, 2013

(54) METHOD AND APPARATUS FOR ENHANCED SIZE REDUCTION OF PARTICLES

(75) Inventors: Boris Y. Shekunov, Aurora, OH (US); Pratibhash Chattopadhyay, North Royalton, OH (US); Jeffrey S. Seitzinger, Broadview Heights, OH (US); Robert W. Huff, North Royalton, OH (US)

(73) Assignee: Ferro Corporation, Cleveland, OH (US)

( * ) Notice: Subject to any disclaimer, the term of this patent is extended or adjusted under 35 U.S.C. 154(b) by 2190 days.

(21) Appl. No.: 10/541,909

(22) PCT Filed: Feb. 24, 2004

(86) PCT No.: PCT/US2004/005412
§ 371 (c)(1),
(2), (4) Date: Dec. 12, 2005

(87) PCT Pub. No.: WO2005/025728
PCT Pub. Date: Mar. 24, 2005

(65) Prior Publication Data
US 2006/0104916 A1    May 18, 2006

Related U.S. Application Data

(60) Provisional application No. 60/449,740, filed on Feb. 24, 2003.

(51) Int. Cl.
*A61K 9/14* (2006.01)
*B29B 9/00* (2006.01)

(52) U.S. Cl.
USPC .............................. 424/489; 264/5

(58) Field of Classification Search
None
See application file for complete search history.

(56) References Cited

U.S. PATENT DOCUMENTS

| 3,323,946 | A | * | 6/1967 | Ravve et al. ................. 427/386 |
| 5,001,224 | A | * | 3/1991 | Barstow et al. .............. 530/334 |
| 5,548,004 | A | | 8/1996 | Mandel et al. |
| 5,716,558 | A | * | 2/1998 | Nielsen et al. ................. 264/13 |
| 5,766,637 | A | | 6/1998 | Shine et al. |

(Continued)

FOREIGN PATENT DOCUMENTS

JP    07196840 A  *  8/1995

OTHER PUBLICATIONS

Chattopadhyay, P. and Gupta, R., Production of Antibiotic Nanoparticles Using Supercritical $CO_2$ as Antisolvent with Enhanced Mass Transfer, Ind. Eng. Chem. Res., 2001, vol. 40, pp. 3530-3539.

(Continued)

*Primary Examiner* — Carlos Azpuru
*Assistant Examiner* — Casey Hagopian
(74) *Attorney, Agent, or Firm* — Rankin, Hill & Clark LLP

(57) ABSTRACT

The present invention provides methods and apparatus for producing particles via supercritical fluid processing. In one embodiment, the method includes expanding a supercritical fluid plasticized melt across a pressure drop to form solid composite particles that are simultaneously dispersed, foamed and cooled, and milling the solid particles produced to achieve the desired size distribution. In another embodiment, a pressure vessel containing a supercritical fluid plasticized melt is depressurized to form a cooled solid porous mass, which is then milled to obtain solid composite particles.

6 Claims, 3 Drawing Sheets

(56) References Cited

U.S. PATENT DOCUMENTS

| | | | |
|---|---|---|---|
| 5,821,175 A * | 10/1998 | Engelsberg | 438/795 |
| 6,284,302 B1 | 9/2001 | Berger et al. | |
| 6,414,050 B1 | 7/2002 | Howdle et al. | |
| 6,426,136 B1 * | 7/2002 | Rouse et al. | 428/327 |
| 6,620,351 B2 | 9/2003 | Gupta et al. | |
| 6,680,110 B1 * | 1/2004 | Deeb et al. | 428/327 |

OTHER PUBLICATIONS

Chattopadhyay, P. and Gupta, R., Protein Nanoparticles Formation by Supercritical Antisolvent with Enhanced Mass Transfer, AIChE Journal, Feb. 2002, vol. 48, No. 2, pp. 235-244.

Supplementary European Search Report for corresponding EP 04809300.0 mailed Jan. 5, 2012, three pages.

* cited by examiner

METHOD AND APPARATUS FOR ENHANCED SIZE REDUCTION OF PARTICLES

BACKGROUND OF THE INVENTION

1. Field of Invention

The present invention relates generally to methods and apparatus for producing particles, and particles formed thereby.

2. Description of Related Art

The enhanced mass-transfer properties and benign nature of supercritical fluid, near-critical fluid and/or compressed gas (hereinafter collectively referred to as "supercritical fluid"), makes it particular suitable for use in the production of particles. One prior art technique, which is often referred to in the art as Particles from Gas-Saturated Solutions (PGSS), employs supercritical fluid for this purpose.

In the conventional PGSS process, supercritical fluid is used to plasticize a material thereby forming a melt. The melt thus formed is then expanded across a pressure drop. As the melt expands, the supercritical fluid changes phase and diffuses out of the melt as a gas, which leads to the formation of particles. A conventional PGSS process is described in U.S. Pat. No. 5,766,636, which is hereby incorporated by reference in its entirety. Advantages of the PGSS process include low processing temperatures for thermally labile compounds, relatively easy scalability and one step processing of particles.

A significant disadvantage of the conventional PGSS process is that it often is not sufficient to lower the viscosity of the melt. This is especially problematic with the processing of many high molecular weight polymers. Because the viscosity of the melt is not sufficiently low and the concentration of the supercritical fluid in the melt is not sufficiently high at feasible operating conditions (i.e., a temperature below about 373 Kelvin (K) and a pressure below about 30 megaPascal (MPa)), efficient particle dispersion and size reduction is difficult.

A particle production technique having benefits of conventional PGSS processing but having improved processability is desirable.

BRIEF SUMMARY OF THE INVENTION

The present invention provides methods and apparatus for producing composite particles using supercritical fluid. In accordance with a first method of the invention, a load stock comprising an excipient and a biologically active substance is contacted with a supercritical fluid to form a melt. The melt is expanded across a pressure drop, which causes at least a portion of the supercritical fluid to diffuse out of the melt. The diffusion of supercritical fluid out of the melt causes the melt to break into smaller particles and solidify practically simultaneously. The expansion of the supercritical fluid is the force for this particle micronization and also produces a porous network within the solid particles (i.e., foaming). In some cases, a rapid temperature decrease can also contribute to a thermal fracture of the solidified particles into smaller particles. For example, the expansion of a melt plasticized with supercritical carbon dioxide ($CO_2$) will chill the resulting particles to a temperature below 0° C. due to the Joule-Thomson effect. In some cases, depending upon the temperature and amount of $CO_2$ present, dry ice (solid $CO_2$) can be formed. Further, the average particle size of the solid particles is reduced using a suitable milling device, preferably before the temperature of the solid particles is permitted to return to ambient temperature. More preferably, the milling step is performed before the temperature of the solid particles is permitted to rise to or above 0° C. Dry ice can be used as an aid in cooling and micronizing the solid particles.

In a second alternative embodiment of the invention, supercritical fluid is used to plasticize a load stock in a vessel. Instead of passing the melt across a pressure drop, the vessel is rapidly depressurized. Depressurization of the vessel causes the supercritical fluid to diffuse from the melt resulting in the formation of a solid, porous mass. Depressurization of the vessel also results in a rapid temperature reduction. For example, the expansion of supercritical $CO_2$ from a plasticized load stock can result in the formation of a porous, solid mass and dry ice. The porous, solid mass and the dry ice can then be milled using a suitable milling device before the temperature of the solid mass is permitted to return to ambient temperature. The milling device, such as grinding rotors, rollers or balls, can be incorporated into the vessel so that the micronization process can occur immediately after the expansion. The alternative embodiment of the invention is particularly suitable for forming solid particles from materials that have too high of a viscosity when plasticized to be efficiently dispersed through an expansion nozzle.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
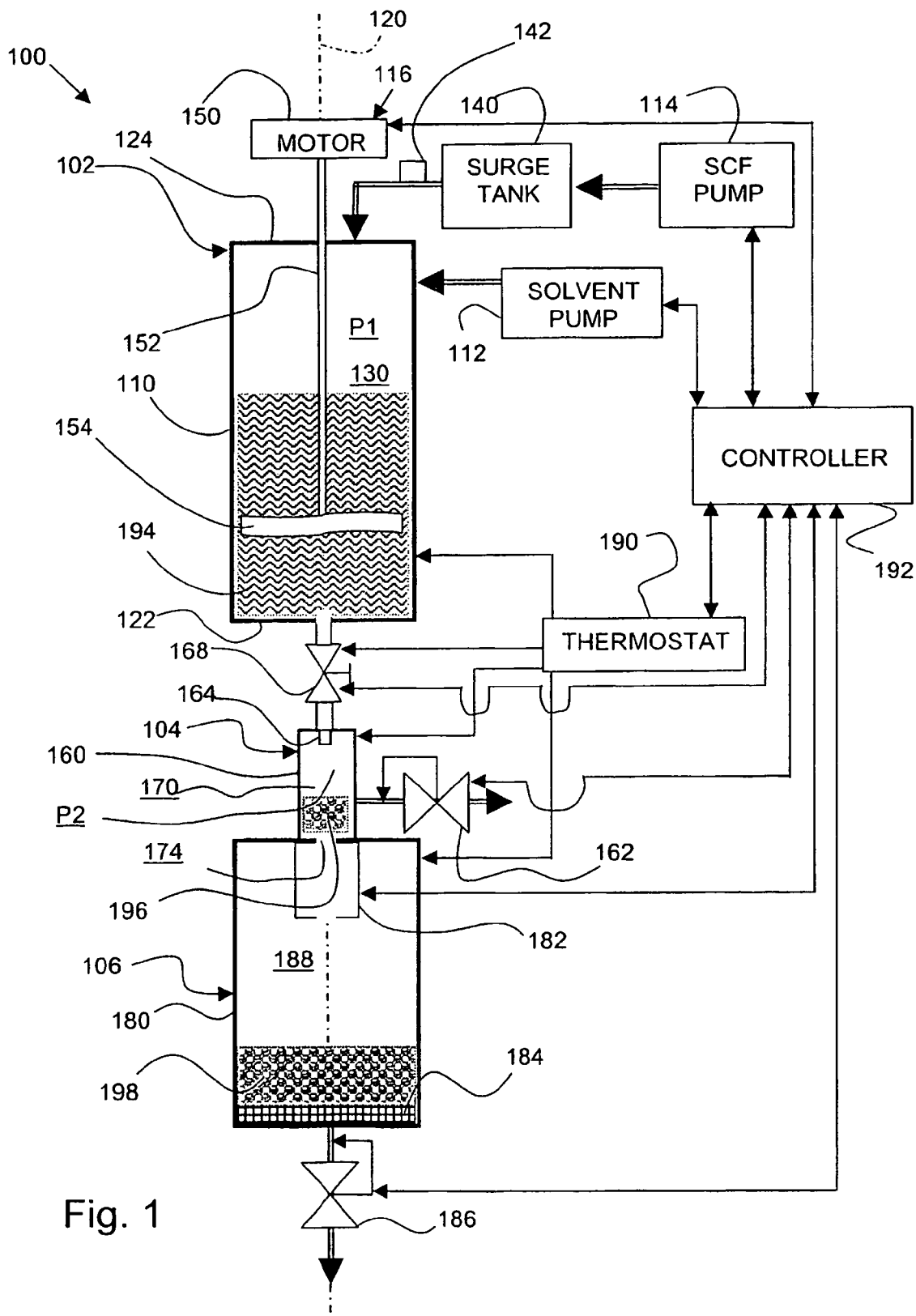
FIG. 1 is a schematic representation of an apparatus for use in carrying out the method of the invention.

The present invention provides a method and an apparatus for producing solid particles. In accordance with the method of the invention, a load stock comprising an excipient and a biologically active substance is plasticized using supercritical fluid to form a melt. The term "melt" as used in this context denotes that the supercritical fluid diffuses into the load stock and thereby reduces its viscosity (e.g., via plasticization, swelling or dissolution) so as to render it fluid or semi-fluid, which can be further processed as such. In some embodiments of the invention, the melt can be flowed, pumped or sprayed as a fluid or semi-fluid. The supercritical fluid dissolves into the load stock causing it to liquefy or plasticize into a melt at temperatures preferably lower than the melting point or glass transition temperature of the components of the load stock.

In a first embodiment of the invention, the supercritical fluid-saturated melt is expanded across a pressure drop, typically through a nozzle. Expansion of the melt across the pressure drop causes the supercritical fluid to undergo a phase change (from a supercritical fluid phase to a gaseous phase), thereby causing the gas to escape and the melt to solidify into solid particles, often having a porous structure. The expansion of the supercritical fluid reduces the temperature of the solid particles. In some cases, the temperature of the particles is reduced to below 0° C., and more preferably, substantially below 0° C.

The solid particles are transferred, either directly or indirectly, into a milling device. The milling device may or may not be a part of the same vessel where the expansion of the supercritical fluid takes place. The milling devices mills or comminutes the solid particles into finer particles of near uniform shape and size. Milling is preferably accomplished before the temperature of the solid particles is permitted to rise to ambient temperature. More preferably, milling is performed before the temperature of the solid particles is permitted to rise to or above 0° C. Most preferably, the solid particles formed during the expansion step are directly transferred to the milling device at the low temperature produced during expansion.

Because the temperature of the solid particles is low, and because the solid particles tend to be porous, the solid particles can be efficiently milled or comminuted into smaller particles of near uniform shape and size. In some instances, it is advantageous for a portion of the supercritical fluid to freeze into a solid form, which can be used as a milling media during the solid particle reduction step. Dry ice, for example, can be formed upon the expansion of supercritical $CO_2$, which can be used to keep the temperature of the solid particles very low and also as a milling media.

The excipient present in the solid particles protects the biologically active substance from local heating and shearing during milling, thus facilitating the micronization of the biologically active substance.

In a second embodiment of the invention, which is suitable for use with highly viscous melts that are difficult to pump through a nozzle across a pressure drop, a solid porous and brittle mass can be formed by contacting a load stock with supercritical fluid in a pressure vessel to form a plasticized melt. The vessel can then be depressurized at a rapid rate. The depressurization of the vessel decreases the temperature within the vessel. Depressurization of the vessel allows the supercritical fluid to undergo a phase change, which results in the formation of a solid porous mass (e.g., foam), which may be a single chunk or several fractured chunks. The low temperature, which is preferably below 0° C., makes the solid porous mass brittle. The solid porous mass is then transferred to a milling device, preferably at the same low temperature as obtained during expansion, and milled to form particles that have a near uniform size and shape. In this case, the milling device can be a part of the same expansion vessel so that materials can be milled immediately after expansion.

A schematic system or apparatus 100 for implementing the method according to the invention is shown in FIG. 1. The apparatus 100 includes a mixing assembly 102, an expansion assembly 104, and a milling assembly 106. The mixing assembly 102 includes a mixing vessel 110, a solvent pump 112, a supercritical fluid pump 114, and a mixer 116.

The mixing vessel 110 is preferably tubular and defines an axis 120, and has first and second ends 122, 124 that are spaced axially apart. Preferably, the axis 120 is oriented vertically such that the first end 122 is below the second end 124. That is, the second end 124 is UP and the first end 122 is DOWN when moving along the axis 120. The mixing vessel 110 has an inner surface that defines a mixing chamber 130. The pressure in the mixing chamber 130 is denoted with the reference number P1. The mixing assembly 102 has means, not shown, for accessing the interior of the mixing vessel 110 so as to charge the interior with a load stock.

As previously noted, the load stock comprises an excipient and a biologically active substance. Throughout the instant specification and in the appended claims, the term "excipient" refers to any one or a combination of generally inert, natural or synthetic substances that are used in the pharmaceutical industry as binders and/or carrier materials for biologically active substances. Suitable excipients for use in the invention include, for example, polymers, waxes, lipids and combinations thereof. The excipient or excipients used in the invention are preferably solids at 25° C. and 1 atmosphere pressure. Suitable polymers for use in the invention include, for example, polysaccharides, polyesters, polyethers, polyanhydrides, polyglycolides (PLGA), polylactic acid (PLA), polycaprolactone (PCL), polyethylene glycol (PEG) and polypeptides. Suitable lipids include, for example, glycerides. Examples of "biologically active substances" include, for example, drugs, peptides, proteins, pharmaceuticals, biopharmaceuticals and therapeutic agents.

In the preferred embodiment of the invention, the biologically active substance is incorporated with the excipient in a desired manner to form a coated, encapsulated or taste-masked formulation, or a controlled prolonged or sustained release formulation. It will be appreciated that the load stock can also further comprise other substances such as, for example, pigments, sugars, diagnostic aids and/or markers, nutritional materials, proteins, peptides, animal and/or plant extracts, dyes, antigens, catalysts, nucleic acids and combinations thereof.

The load stock must be capable of forming a melt when contacted with a supercritical fluid under pressure. Throughout the instant specification and in the appended claims, the term "melt" denotes that the supercritical fluid reduces the viscosity of the load stock (e.g., via plasticization, swelling or dissolution) so as to render it a fluid or semi-fluid that can be processed as such. In other words, the load stock can be flowed, pumped or sprayed as a fluid or semi-fluid.

The supercritical fluid pump 114 is preferably a P-200 high-pressure reciprocating pump commercially available from Thar Technologies, Inc. (Pittsburgh, Pa.). Suitable alternative pumps include diaphragm pumps and air-actuated pumps that provide a continuous flow of supercritical fluid. The high-pressure pump 114 preferably comes factory-equipped with a burst-type rupture disc, manufactured by Fike Inc. (Blue Springs, Mo.), which is plumbed into a pressure relief system.

The supercritical fluid pump 114 pumps supercritical fluid through a surge tank 140 and a metering valve 142 so as produce a pulse-free flow. Because the supercritical fluid pump 114 is in fluid communication with the mixing chamber 130, the supercritical fluid pump 114 can supply supercritical fluid through the surge tank 140 into the chamber 130.

With reference to the supercritical fluid that the supercritical fluid pump 114 supplies to the chamber 130, as noted hereinabove and used herein "supercritical fluid" includes not only supercritical fluid, but also compressed gas and liquefied gas, and other materials suitable, for example, to form a melt as described herein. The supercritical fluid is preferably supercritical carbon dioxide ("$CO_2$"). Suitable alternative fluids include, nitrous oxide, dimethylether, straight chain or branched C1-C6-alkanes, alkenes, ethane, propane, fluoroform, chlorotrifluoromethane, chlorodifluoromethane, propylene, ammonia and combinations thereof. Preferred alkanes include ethane, propane, butane, isopropane, and the like.

The supercritical fluid is chosen generally with reference to the ability of the supercritical fluid to melt, swell or plasticize the load stock during a mixing and melt formation operation. The freezing or solidification point of the supercritical fluid is also a factor in selecting the supercritical fluid for use in a method according to the present invention.

The mixer apparatus 116 includes a motor 150, a shaft 152 extending from the motor 150 through the second end 124 of the mixing vessel 110 and into the chamber 130, and a rotor 154 disposed at a distal end of the shaft 152 and located in the chamber 130. The mixing rate is controlled by the rotation speed and geometry (type and diameter) of the rotor 154. The rotor 154 is preferably a propeller-shaped two-bladed mixer. Additional, supplemental and alternative mixing methods include both static and moving mixing devices, such as baffles, rotors, turbines, shear-mixers, ultrasonic devices, and other devices or mechanisms used to mix the contents of the mixing assembly 102.

With reference to the expansion assembly 104, the expansion assembly 104 communicates with the mixing assembly 102 via a release valve 168. The release valve 168 is preferably a model R3A ¼" proportional pressure release valve, which is commercially available from Swagelok, Inc. (Solon, Ohio). The release valve 168 is actuated by system pressure acting against a spring, and is capable of reseating. Additional release valves (not shown) are located in regions of the system 100 which are isolatable between two other valves, and are piped into a dedicated relief venting system. The release valve 168 is thus disposed between the mixing vessel 110 and the expansion vessel 160, and is in fluid communication with a nozzle 164.

In order to pass the melt across a pressure drop as described in the first method of the invention, the expansion assembly 104 preferably includes a receiving or expansion vessel 160, which is preferably tubular, a backpressure regulator 162 and a nozzle 164. The expansion vessel 160 has an inner surface that defines an expansion chamber 170. The pressure inside the expansion chamber is denoted with reference number P2. The expansion vessel 160 has an outlet 196 that opens directly into the milling assembly 106. The solid particles can be transferred into the milling assembly 106 directly from the expansion chamber while still under the influence of the temperature reduction. The supercritical fluid can behave as both a transporting medium both by maintaining particle flow through the milling device, and as a heat sink or temperature modifier.

Preferably, the supercritical fluid-saturated melt is expanded directly into the milling device. Where an expansion vessel that is separated from the milling device is used, the melt is expanded into the expansion chamber and then communicated to the milling device while still at the reduced temperature. The solid particles can be transferred into the milling assembly 106 directly from the expansion chamber while still under the influence of the temperature reduction. The supercritical fluid can behave as both a transporting medium both by maintaining particle flow through the milling device, and as a heat sink or temperature modifier.

The backpressure regulator 162 is preferably a model 26-1700 regulator, which is commercially available from Tescom, USA (Elk River, Minn.). The backpressure regulator 162 maintains the pressure P2 in the expansion chamber 170 in a predetermined range of pressures during operation of the apparatus 100.

The milling assembly 106 communicates with the expansion assembly 104 via the outlet 174 from the expansion assembly 104. The milling assembly 106 includes a milling vessel 180, a milling device 182, a filter 184, and optionally a second backpressure regulator 186. The milling vessel 180 has an inner surface that defines a mill chamber 188. The milling device 182 is disposed within the mill chamber 188 and communicates with the outlet 174. Accordingly, material from the expansion chamber 170 can flow into the milling device 182 through the outlet 174, and preferably directly into the milling device 182.

The milling device 182 is preferably is a jet mill or a COMIL model cryogenic mill, which is commercially available from Quadro, Inc. (Milburn, N.J.). Other suitable size reducing devices or mills include a high-energy bead mill or attritor mill, rod mill, roller mill, ceramic ball mill, media mill, fluidized energy mill, cryogenic comminuter, ultrasonic comminuter, grinder, and the like.

The filter 184 is disposed adjacent to the second backpressure regulator 186. The filter 184 can block solid material from flowing into the second backpressure regulator 186. A thermostat 190 communicates with heating elements (not shown) that are located proximate to the mixing vessel 110, the expansion vessel 160, the milling vessel 180, and the release valve 168. A controller 192 communicates with and controls the solvent pump 112, the supercritical fluid pump 114, the thermostat 190, the mixer apparatus 116, the backpressure regulators 162, 186, the milling device 182, and the release valve 168. Standard controllers are commercially available, and are interchangeable therewith.

Figure 2:
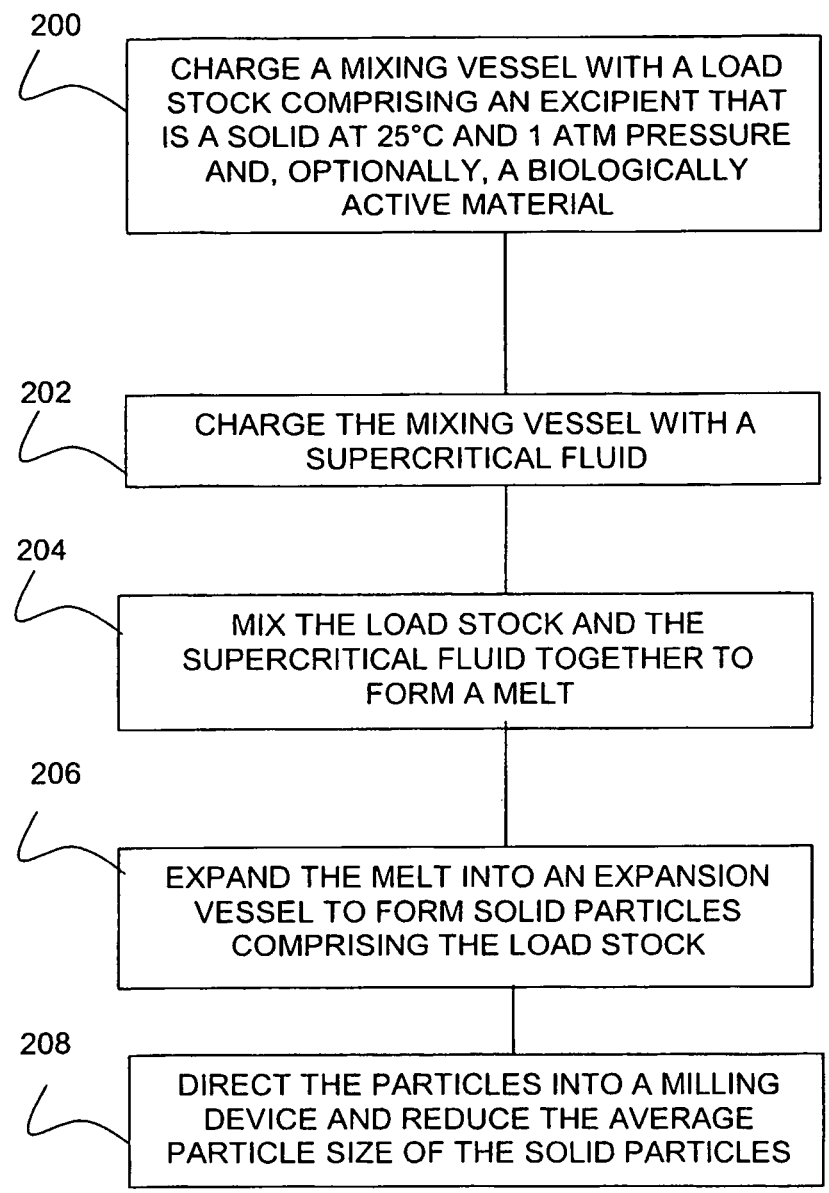
FIG. 2 is a block diagram of the steps of a method according to the invention.
Figure 3:
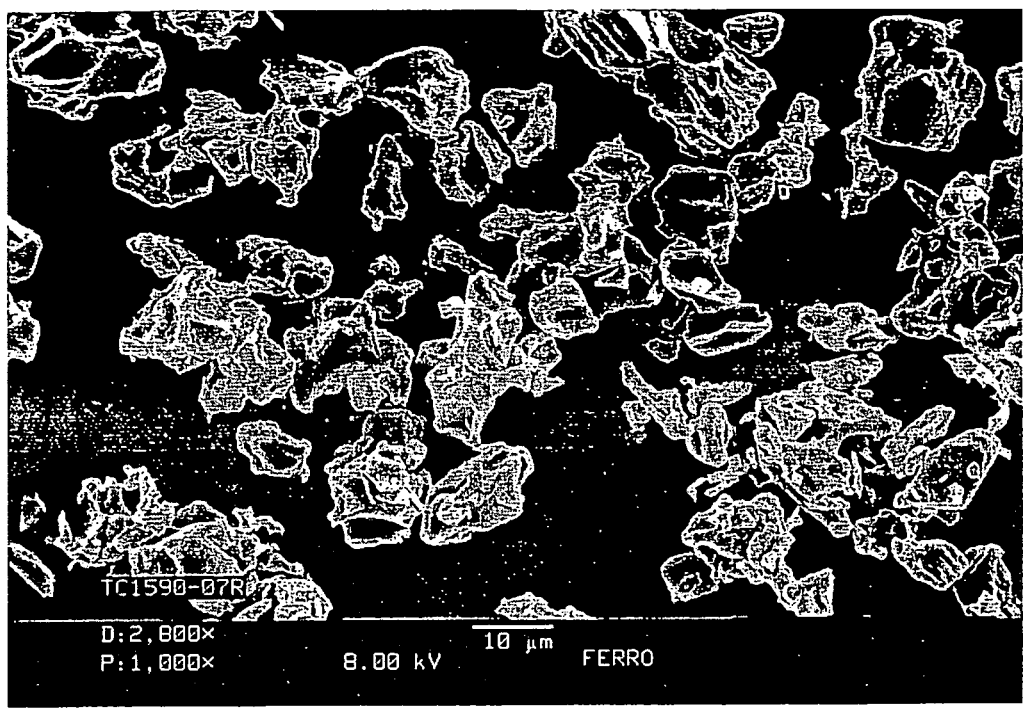
FIG. 3 is a scanning electron micrograph of the particles produced in Example 1.

Thus, the first embodiment of the method of the invention involves charging the mixing vessel 102 with a load stock comprising an excipient that is a solid at 25° C. and 1 atmosphere pressure and a biologically active substance (see FIG. 2, step 200). The controller 192 activates the supercritical fluid pump 114 to supply a quantity of supercritical fluid through the surge tank 140, through the metering valve 142, and into the mixing chamber 130 (step 202). The addition of supercritical fluid increases the pressure P1 in the mixing chamber 130. The thermostat 190 and the supercritical fluid pump 114 cooperate to maintain the temperature and the pressure P1, respectively, in a generally constant operating range. Accordingly, the pressure P1 is generally in a range that is increased relative to atmospheric pressure. Preferably, the supercritical fluid is maintained in the predetermined range such that the supercritical fluid remains in a supercritical state.

The supercritical fluid contacts the load stock in the mixing chamber 130. The controller 192 controls the mixer apparatus 116 to engage the motor 150 so as to rotate the shaft 152. The rotor 154 mixes the supercritical fluid and the load stock together until a uniform mixture is achieved. The load stock forms a melt 190 when mixed with the supercritical fluid under pressure (step 204).

In some cases, it is desirable for the load stock to further comprise a solvent. Solvents can interact with and affect the visco-elastic properties of the load stock and/or the molten mass to enhance mixing and blending in the mixing vessel 110. The solvent can be added to the mixing chamber 130 prior to the introduction of supercritical fluid or, alternatively, can be added using the solvent pump 112 after or during introduction of the supercritical fluid. If desired, excess supercritical fluid can be circulated through the mixing chamber 130 prior to expansion to extract supercritical fluid soluble solvents from the melt, to the extent any are present. Preferably, the solvent is removed before expansion of the melt. The solvent or solvent(s) used in the invention can be organic solvents or inorganic solvents. Examples of suitable solvents include acetone, water, methanol, ethanol, toluene, ethyl acetate, methylene chloride, dimethyl sulfoxide and dimethyl formamide.

The melt 194 is then expanded across a pressure drop (step 206), typically through a nozzle 164, into a collection chamber 160. To facilitate and control the expansion of the melt, the controller 192 controls the backpressure regulator 162 and the release valve 168 to influence the pressure P2 in the expansion chamber 170. Thus, the pressure P2 is preferably increased relative to atmospheric pressure, but decreased relative to the pressure P1 in the mixing chamber 130. Because the pressure P1 in the mixing chamber 130 is greater than atmospheric pressure, increasing the pressure P2 in the expansion chamber 170 reduces the size of the pressure differential between the pressures P1, P2 in the chambers 130, 170. By affecting the pressure differential, the size and morphology of the resultant solid particles can be controlled. Generally, the larger the pressure differential the smaller the resultant solid particles that are produced.

The controller 192 controls the release valve 168 to switch from a closed condition to an open condition. In response to the opening of the release valve 168, and under the influence of the pressure differential between the chambers 130, 170, the melt 194 flows through the release valve 168 and further though the nozzle 164. The pressurized melt 194 is sprayed from the nozzle 164 either into the chamber or directly into the milling device 170. Because of the pressure reduction of the melt 194 during expansion (from the pressure P1 in the mixing chamber 130 to the relatively lower pressure P2 in the expansion chamber), the supercritical fluid contained in the melt 194 diffuses out of the melt and thereby increases the melt point and/or glass transition temperature of the melt 194, decreases the temperature of the melt 194, and expands to increase the volume of the melt 194.

In response to the expansion, the melt 194 solidifies into solid particles 196 comprising the load stock (step 206). The phase change of the supercritical fluid from liquid to gas reduces the localized temperature of materials adjacent to the expansion location (i.e., at the nozzle outlet). Further, a portion of the supercritical fluid may crystallize or freeze in response to the temperature reduction, as discussed hereinabove. Whether a portion of the supercritical fluid crystallizes is determined by factors such as the selection of supercritical fluid, and the temperature and pressure of the expansion chamber during operation. The solid particles will have a temperature below 0° C.

In addition, any other materials that were added to the melt 194, for example, during the mixing and formation of the melt 194 (reference step 204), are also formed or are co-precipitated into the solid particles 196. For example, if any materials are dissolved, and/or suspended in the supercritical fluid, the dissolved or suspended materials precipitate or solidify during the expansion and phase change of the supercritical fluid. The solid particles 196 can thus form composite solid particles that collect in the expansion chamber 170. Accordingly, the solid particles can be microspheres or microcapsules, and the like. Rather than discrete solid particles, the expanded material can be precipitated as a suspension, a foam, a web, or a gel, and the solid particles can have different surface profiles or morphologies or can be grouped or agglomerated. The solid particles 196 form a suspension in the solvent if the solvent is not removed during the mixing or the expansion step.

In the first embodiment of the invention, the solid particles 196 are immediately directed into the milling device 182 (step 208). Alternatively, the solid particles 196 are milled in a separate milling device. In addition, the milling device can be incorporated into the mixing chamber 130, so that the entire batch can be milled without transferring the solid material into a separate milling apparatus. The milling device 182 grinds, comminutes or micronizes the solid particles 196 to reduce their average particle size before the temperature of the solid particles is permitted to rise above 0° C. It will be appreciated that grinding may cause the temperature of the solid particles to increase above 0° C., but the temperature of the solid particles must be below 0° C. when the grinding operation commences. Preferably, frozen fluid particles are present during grinding, and are co-micronized by the milling device 182. The fluid particles act as grinding media to further enhance the size reduction or morphology of the solid particles 196.

In the second embodiment of the invention for cases where the melt viscosity is high, the melt is first converted into a low temperature solidified porous mass by rapid depressurization of the mixing vessel. The mass thus obtained is collected from the mixing vessel then communicated into a separate milling device to form fine uniform sized particles. The mixing vessel used here is similar to the one descried in the earlier embodiment.

Preferably, micronized solid particles 198 having a narrow size distribution and a mean size in a range of from about 0.1 μm to about 500 μm are collected in the milling chamber 188. By varying the process conditions, it is possible to obtain particles having a desired mean size within a desired particle size distribution for particular pharmaceutical applications and/or drug delivery routes. The micronized solid particles 198 are then brought to ambient temperatures and pressures. As a result of the change in the temperature and/or pressure, frozen fluid particles, if present, sublime and are removed or separated from the micronized solid particles 198. If solvent, surfactant or other undesirable processing aid is present in the micronized solid particles 198, the micronized solid particles 198 can be filtered and/or washed to remove the solvent, surfactant and/or aid.

Accordingly, the advantages of expanding the melt with a supercritical fluid, and of milling a mixture of solid particles and solid and frozen fluid particles, are obtained with a reduced reliance on the particle micronization during expansion through the nozzle, the diffusion rates of supercritical fluid from the melt and the shear stresses experienced during flow through the nozzle. Solidified fluid particles present, helps maintain a reduced temperature during milling following the expansion stage. The porous structure of such particles greatly enhances the milling process. Further more, the excipient present in the composite solid particles helps protect the biologically active substance from local heating and shear stresses during milling. These factors help preserve the stability of thermally labile and shear-labile biologically active substances such as, for example, peptides and proteins.

The following examples are intended only to illustrate the invention and should not be construed as imposing limitations upon the claims. Unless specified otherwise, all ingredients are commercially available from such common chemical suppliers as Sigma Aldrich, Inc. (St. Louis, Mo.) and/or Fisher Scientific International, Inc. (Hanover Park, Ill.).

EXAMPLE 1

Preparation.

Initially, 5 grams (g) of EUDRAGET RS100 and 1.6 g acetaminophen (paracetamol) were dissolved into 15 milliliters (ml) of acetone. The solution was charged to a mixing vessel. The mixing vessel defined a chamber having a volume of 100 ml and had a diameter of 32 millimeters (mm). The chamber was pressurized with carbon dioxide gas ($CO_2$) to an operating pressure of 30 megaPascal (MPa), and heated to a temperature of 323 Kelvin (K).

At the predetermined temperature and pressure, the carbon dioxide became supercritical. The controller was set to maintain the mixer to rotate the mixer blade at a constant agitation speed of 4000 revolutions per minute (rpm). The ingredients were mixed for 30 minutes.

Carbon dioxide was circulated through the mixing vessel during the mixing stage. The circulating carbon dioxide removed the acetone from the solution, thus forming a residual homogeneous mass or melt of acetaminophen crystals and EUDRAGIT carrier.

Expansion of Particles.

A release valve was opened to communicate the contents of the mixing vessel, i.e. the melt, to an expansion vessel. Specifically, the release valve communicated the mixture to a nozzle that opened into the interior of the expansion vessel with an excess of carbon dioxide. The nozzle had an orifice with a diameter of 1.19 millimeter (mm). The pressure in the interior of the expansion vessel was above standard atmospheric pressure, but below 30 MPa. The pressure in the mixing vessel was adjusted to remain at a constant 30 MPa. The expansion caused both a pressure reduction and a temperature reduction. As a result of the pressure reduction, a portion of the carbon dioxide phase changed to a gas and supersaturated the melt. In response to the supersaturation, the melt formed or precipitated into solid particles. As a result of the temperature reduction, another portion of the carbon dioxide formed into frozen supercritical fluid particles. The frozen supercritical fluid particles and solid particles were intimately mixed during the respective formations.

The solid particles and frozen supercritical fluid particles were collected and directed into a mill. The mill was a rotary grinder operating at a speed of 10,000 revolutions per minute (RPM). The solid particles and the frozen supercritical fluid particles were ground together and collected into the mill vessel bottom.

Analysis of the Particles.

Analysis of the particles was performed using a Scanning Electron Microscope (SEM) to determine size and morphology, using an X-ray powder diffraction spectrometer (XPD) to determine solid phase/crystallinity, and using a laser diffraction particle analyzer to determine particle size distribution.

The particles produced had a mean particle diameter of 18.4 micrometers (µm). X-ray phase analysis determined that more than 90% of the acetaminophen was contained in the crystalline form coated by amorphous EUDRAGET polymer.

EXAMPLE 2

Preparation.

Initially, 10 grams (g) of Polyester was loaded into the mixing vessel described in Example 1. The vessel was pressurized with carbon dioxide gas ($CO_2$) to an operating pressure of 30 megaPascal (MPa), and heated to a temperature of 333 (K). The controller was set to maintain the mixer to rotate the mixer blade at a constant agitation speed of 2000 revolutions per minute (rpm). The polymer was mixed for 30 minutes.

Expansion.

A release valve was opened at the top of the mixing vessel to reduce the pressure of the mixture from 30 MPa to 1 bar for about 10 s. The expansion caused both a pressure reduction and a temperature reduction. The melt formed a porous mass of polymer and dry ice.

The resulting porous solid was collected and directed into a rotary grinder operating at a speed of 10,000 revolutions per minute (RPM). For comparison, solid untreated polymer in the form of flakes (between 1-2 mm size) was mixed with dry ice and subjected to the same micronization procedure.

Analysis of the Particles.

Analysis of the particles was performed using a Scanning Electron Microscope (SEM) to determine size and morphology and laser diffraction particle analyzer to determine particle size distribution.

The particles produced from processed polyester had a mean particle diameter of 8 micrometers (µm) when compared to about 13 µm for the starting material. It is shown, that a single stage milling according to the present invention generated particles that were significantly smaller than those produced by conventional cryogenic milling of the rough material. The SEM photographs showed an extended porous network produced by the $CO_2$ fluid escape, which facilitated smaller particle sizes and a more uniform particle size distribution of the processed material.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of producing solid particles comprising the steps of:
   providing a load stock comprising:
      an excipient that is a solid at 25° C. and 1 atmosphere pressure; and
      optionally, a biologically active substance;
   contacting the load stock with a supercritical fluid in a pressure vessel that is pressurized and heated to maintain said fluid supercritical, and to form a melt;
   depressurizing the pressure vessel to transform the melt in the pressure vessel into a solid porous mass that is cooled to a temperature below 25° C.; and
   milling the solid porous mass to obtain solid particles.

2. The method according to claim 1 wherein the solid porous mass is milled before the temperature of the solid porous mass is permitted to rise to 25° C.

3. The method according to claim 1 wherein subsequent to the milling step the solid particles have an average particle size of from about 0.1 to about 500 micrometers (µm).

4. The method according to claim 1 wherein the excipient is a polymer selected from the group consisting of polysaccharides, polyesters, polyethers, polyanhydrides, polyglycolides, polylactic acids, polycaprolactones, polyethylene glycols and polypeptides.

5. The method according to claim 1 wherein the supercritical fluid is selected from the group consisting of carbon dioxide, water, nitrous oxide, dimethylether, straight chain or branched $C_1$-$C_6$-alkanes, alkenes, alcohols, ethane, propane, fluoroform, chlorotrifluoromethane, chlorodiflueromethane, propylene, ammonia and combinations thereof.

6. The method according to claim 1 wherein the supercritical fluid is carbon dioxide.

* * * * *